US00PP20302P2

(12) United States Plant Patent
Bremner

(10) Patent No.: US PP20,302 P2
(45) Date of Patent: Sep. 15, 2009

(54) ***POTENTILLA* PLANT NAMED 'SUMMER DAWN'**

(50) Latin Name: *Potentilla ILLA fruticosa*
Varietal Denomination: SUMMER DAWN

(76) Inventor: Alan Heddle Bremner, Bendigo St. Ola, Kirkwall, Orkney (GB), KW15 1SX ( * ) Notice: Subject to any disclaimer, the term of this patent is extended or adjusted under 35 U.S.C. 154(b) by 3 days.

(21) Appl. No.: 12/154,186

(22) Filed: May 19, 2008

Related U.S. Application Data

(60) Provisional application No. 60/932,323, filed on May 29, 2007.

(51) Int. Cl.
*A01H 5/00* (2006.01)

(52) U.S. Cl. ..... Plt./237

(58) Field of Classification Search ..... Plt./237
See application file for complete search history.

*Primary Examiner*—June Hwu

(57) ABSTRACT

A new cultivar of *Potentilla* plant named 'Summer Dawn' that is characterized by compact habit even after twenty years, dense grey-green foliage, and large primrose yellow flowers. In combination these traits set 'Summer Dawn' apart from all other varieties of *Potentilla* known to the inventor.

2 Drawing Sheets

Genus: *Potentilla.*
Species: *fruticosa.*
Denomination: 'Summer Dawn'.

BACKGROUND OF THE INVENTION

The present invention relates to a new and distinct cultivar of *Potentilla,* commonly known as Bush Cinquefoil, or Shrubby *Potentilla,* which is grown as a dwarf summer-flowering shrub for use in the garden and landscape. The new cultivar is known botanically as *Potentilla fruticosa,* and will be referred to hereinafter by the cultivar name 'Summer Dawn'. 'Summer Dawn' arose from a breeding program carried out by the inventor at the inventor's nursery on the Island of Orkney in Scotland, United Kingdom, which the inventor commenced in 1976.

Shrubby *Potentillas* are especially well-adapted to the harsh weather conditions of Orkney which experiences long, dull and wet winters, with salt-laden winds and frequent severe gales. Summers are short and cool, and the prevailing soil type is heavy boulder clay. Although *potentillas* suffer die-back in these conditions, re-growth occurs quickly and flowering occurs and persists during the summer and early autumn months.

Initially, the inventor gathered together approximately sixty named cultivars of *Potentilla,* and planted them in the open ground with the intention of facilitating open pollination. Seed was harvested each autumn and seedlings raised the following spring. As the inventor observed the flowering and plant habit of each new seedling, it was either discarded or re-planted in association with similar selections in order to encourage open pollination within each color group. The initial aim of the breeding program was to produce robust white-flowered forms. More recently the inventor has been interested in producing a collection of new *Potentilla* varieties with novel flower colors and improved plant habit leading to better garden and landscape performance.

'Summer Dawn' was identified and selected in 1985 for its useful combination of attractive pale yellow flowers which are large in comparison with other cultivars of similar color known to the inventor, a long flowering period, and a compact habit without pruning, even after 20 years of observation in the ground.

The male and female parents of 'Summer Dawn' were unnamed, unreleased seedlings which the inventor had raised from previous open pollinations going back to the inventor's original acquisition of named cultivars.

The cultivar of *potentilla* which is considered to be closest in flower color and plant habit to 'Summer Dawn' is the variety 'Primrose Beauty' (unpatented). Whereas 'Primrose Beauty' achieves a height of 1.3 meters to 1.7 meters, and a spread of 2 meters, 'Summer Dawn' has remained compact, not exceeding 1 meter in height and spread, even after 20 years. The diameter of the flowers of 'Primrose Beauty' is 25 mm, whereas the flowers of 'Summer Dawn' are 35 mm–50 mm in diameter.

'Summer Dawn' was first asexually propagated by the inventor in Orkney, Scotland, United Kingdom in summer 1985, by taking softwood cuttings. The plants resulting from this first and from all subsequent generations have grown and flowered uniformly and identically with the inventor's initial selection. The inventor has determined that the new variety 'Summer Dawn' is stable and reproduces true to type in successive generations of asexual propagation.

SUMMARY OF THE INVENTION

The following traits have been repeatedly observed and represent the distinguishing characteristics of the new *Potentilla* cultivar named 'Summer Dawn'. These traits in combination distinguish 'Summer Dawn' from all other varieties of *Potentilla* known to the inventor. The new invention has not been tested under all possible conditions and phenotypic differences may be observed with variations in environmental, climatic, and cultural conditions, however, without any variance in genotype.

1. 'Summer Dawn' is a compact upright bush which eventually attains height of 1 meter and spread of 1 meter after 20 years, without pruning.

2. After three years in a container, 'Summer Dawn' grows to 50 cm. in height and 30 cm. in width.
3. The flowers of 'Summer Dawn' are primrose yellow in color, becoming slightly darker towards the center.
4. The flowers of 'Summer Dawn' are 35 mm to 50 mm in diameter, which is large by comparison with other cultivars known to the inventor.
5. 'Summer Dawn' flowers continually through the summer.
6. 'Summer Dawn' is hardy to USDA Zone 3.

BRIEF DESCRIPTION OF THE DRAWINGS

The accompanying color drawings illustrate the overall appearance of the new *Potentilla* variety named 'Summer Dawn' showing color as true as is reasonably possible to obtain in color reproductions of this type. The plant depicted in the drawings is 3-years-old and growing out-of-doors in Arroyo Grande, Calif.

Drawing labeled

Drawing labeled

Figure 1:
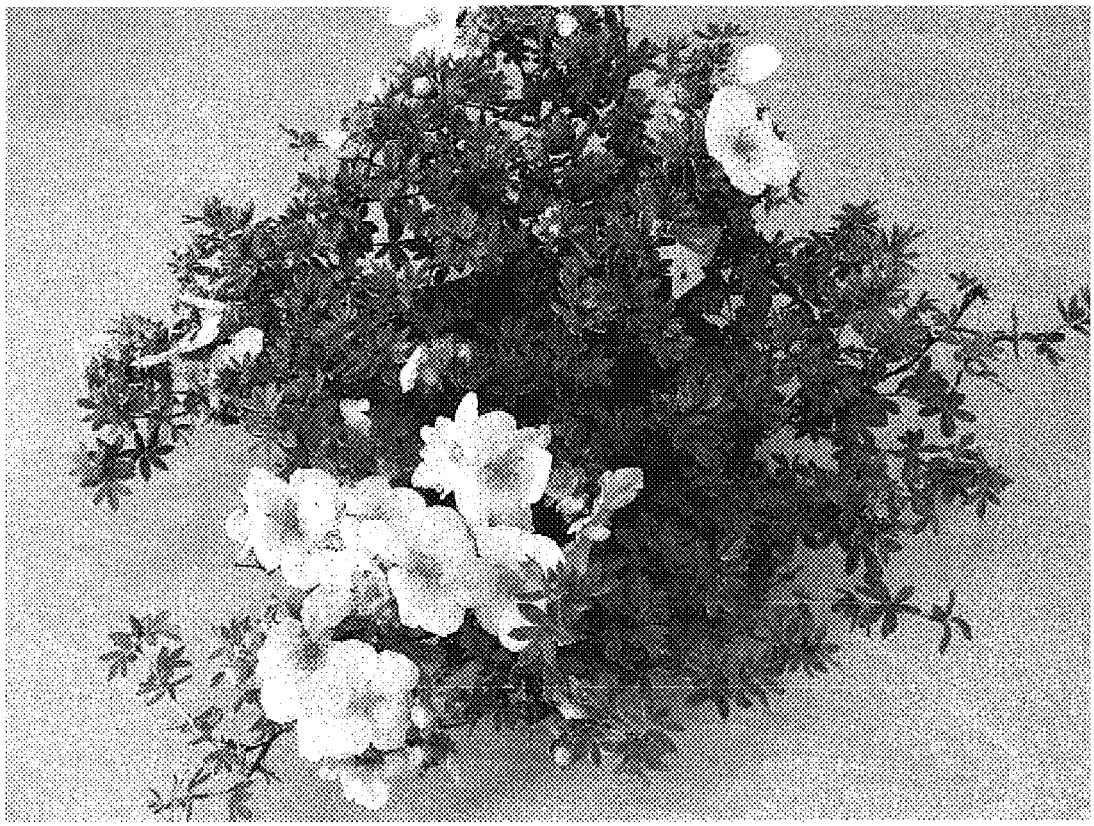
FIG. 1 depicts 'Summer Dawn' in bloom.
Figure 2:
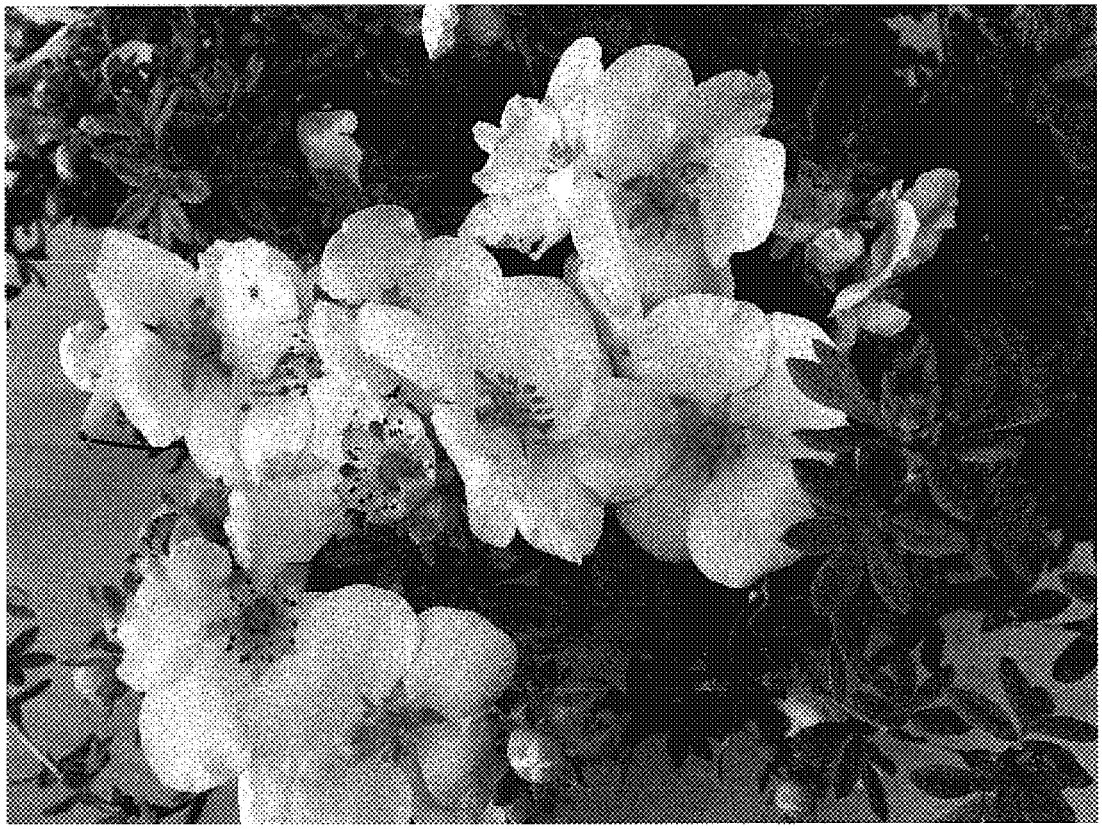
FIG. 2 depicts a close-up view of the flowers.

Color in drawings may differ from color values cited in the detailed botanical description, which accurately describe the actual color of the new variety 'Summer Dawn'. Drawings were made using conventional techniques and although color may appear different from actual color due to light reflectance, they are as accurate as possible by conventional photography.

BOTANICAL DESCRIPTION OF THE PLANT

The following is a detailed description of the new *Potentilla* cultivar named 'Summer Dawn'. Data was collected in Arroyo Grande, Calif. from 3-year-old plants growing out-of-doors. Color determinations are in accordance with The 2001 Royal Horticultural Society Colour chart except where general color terms of ordinary dictionary significance are used. The growing requirements are similar to the species and no disease problems have been observed.

Botanical classification: *Potentilla fruticosa* 'Summer Dawn'.
Family: Rosaceae.
Genus: *Potentilla.*
Species: *fruticosa.*
Denomination: 'Summer Dawn'.
Common name: Cinequefoil.
Parentage: *Potentilla fruticosa* 'Summer Dawn' is a hybrid plant that resulted from open pollination of unnamed and unreleased open pollinated seedlings. The male and female parents are unknown.
Type: Deciduous shrub.
Use: For use in border and landscape.
Commercial classification: Sub-shrub.
Vigor: Low.
Root system: Fine and fibrous.
Habit: Upright.
Height: 50 cm.
Width: 30 cm.
Hardiness: USDA Zone 3.
Seasonal interest: Profuse flowering in spring and summer.
Propagation method: Stem cuttings.
Cultural conditions: Grow in full sun and well-draining soil, with moderate water.
Crop time (range): 9–12 months are needed to produce a finished 1-liter container from a rooted cutting.
Rooting time (average): 8–10 weeks are needed for an initial cutting to produce roots.
Susceptibility to pests and disease: No susceptibility to pests or disease known to the inventor.
Stem:
*Branching.*—Dense lateral branching.
*Main trunk color.*—165A.
*Trunk surface.*—Scurfy.
*Trunk width.*—4 cm.
*Stem shape.*—Subcylindrical.
*Stem color.*—Both 182A and 178A are individually present.
*Stem surface.*—Villous.
*Stem dimensions* (*range*).—18 cm–23 cm. in length and 2 mm. in diameter.
*Internode* (*range*).—1.50 cm–2 cm.
Foliage:
*Type.*—Winter deciduous.
*Leaf arrangement.*—Alternate.
*Leaf division.*—Palmate.
*Leaf dimensions* (*range*).—1.25 cm–2.75 cm. in length and 1.50 cm–3 cm. in width.
*Leaf color* (*abaxial surface*).—N138D.
*Leaf color* (*adaxial surface*).—In the range N138A to N138B.
*Leaf shape.*—Flabellate.
*Leaf attachment.*—Petiolate.
*Petiole shape.*—Cylindrical.
*Petiole color.*—N138D.
*Petiole surface.*—Pubescent.
*Petiole dimensions.*—1.50 cm. in length and 1 mm. in width.
*Leaf margin.*—Divided.
*Leaflets* (*range*).—3–5 in number.
*Leaflet dimensions* (*range*).—1 cm–1.50 cm. in length and 0.40 cm–0.60 cm. in width.
*Leaflet surface* (*abaxial and adaxial*).—Pubescent.
*Leaflet shape.*—Spatulate.
*Leaflet apex.*—Rounded.
*Leaflet base.*—Attenuate.
*Leaf venation.*—Reticulate.
*Vein color* (*abaxial surface*).—N138D.
*Vein color* (*adaxial surface*).—N138D.
*Foliar fragrance.*—None observed.
Flower:
*Inflorescence.*—Solitary.
*Flower arrangement.*—Terminal.
*Flower quantity* (*range*).—50–80 on an individual plant.
*Flower shape.*—Saucer-shaped.
*Flower dimensions.*—1 cm. in depth and 35 mm–50 mm in diameter.
*Aspect.*—Facing upward and outward.
*Self-cleaning or persistent.*—Self-cleaning.
*Flower color.*—The following colors are all present: 1D, 1C, 3B, 3C.
*Petals.*—5 in number.
*Petal dimensions.*—2 cm. in length and 2 cm. in width.
*Petals fused or unfused.*—Unfused.
*Petal margin.*—Entire.
*Petal apex.*—Obtuse.
*Petal base.*—Truncate.
*Petal shape.*—Orbicular.
*Petal surface* (*abaxial and adaxial*).—Glabrous.

*Petal color* (*abaxial surface*).—In the range 1D to 1C.
*Petal color* (*adaxial surface*).—In the range 3B to 3C.
*Bud color.*—3A.
*Bud shape.*—Obovate.
*Bud surface.*—Puberulent.
*Bud dimensions.*—4 mm. in height and 5 mm. in width.
*Bud quantity* (*range*).—50–80 on an individual plant.
*Sepals.*—5 in number.
*Sepals fused or unfused.*—Unfused.
*Sepal margin.*—Entire.
*Sepal apex.*—Apiculate.
*Sepal surface* (*abaxial*).—Villous.
*Sepal surface* (*adaxial*).—Puberulent.
*Sepal color* (*abaxial and adaxial surfaces*).—In the range 182A to 153B.
*Sepal dimensions.*—6 mm. in length and 5 mm. in width.
*Bractlets* (*subtending sepals*).—5 in number.
*Bractlets fused or unfused.*—Unfused.
*Bractlet margin.*—Entire.
*Bractlet apex.*—Apiculate.
*Bractlet surface* (*abaxial*).—Villous.
*Bractlet surface* (*adaxial*).—Puberulent.
*Bractlet color* (*abaxial and adaxial surfaces*).—137B.
*Bractlet dimensions.*—6 mm. in length and 5 mm. in width.
*Calyx dimensions.*—1 cm. in diameter.
*Calyx surface* (*abaxial surface*).—Villous.
*Calyx surface* (*adaxial surface*).—Puberulent.
*Calyx shape.*—Stellate.
*Calyx color.*—182A, 153B, 137B are all individually present.
*Peduncle shape.*—Cylindrical.
*Peduncle surface.*—Villous.
*Peduncle color.*—N144C.
*Peduncle dimensions.*—0.75 cm. in length and <1 mm. in diameter.
*Flower fragrance.*—Delicate scent.

Reproductive organs:
*Stamens.*—About 20.
*Stamen color.*—13A.
*Stamen length.*—2 mm.
*Anther.*—About 20 in number.
*Anther shape.*—Hastate.
*Anther color.*—22A.
*Anther length.*—Less than 1 mm.
*Pollen.*—Low amount.
*Pollen color.*—163C.
*Carpel.*—More than 10.
*Carpel color.*—163A.
*Carpel length.*—Less than 1 mm.
*Ovary position.*—Inferior.
*Ovary color.*—163D.
*Ovary shape.*—Convex.
*Ovary dimensions.*—1 mm. in height and 2 mm. in diameter.

Seed: None observed to date.

What is claimed is:

1. A new and distinct variety of *Potentilla* plant named 'Summer Dawn' as described and illustrated herein.

* * * * *